US00PP12374P2

(12) United States Plant Patent
van Andel

(10) Patent No.: US PP12,374 P2
(45) Date of Patent: Jan. 29, 2002

(54) SPATHIPHYLLUM PLANT NAMED 'JUMBO'

(75) Inventor: Otto Jan Robert van Andel, Kudelstaart (NL)

(73) Assignee: Gebr. Braam, De Kwakel (NL)

( * ) Notice: Subject to any disclaimer, the term of this patent is extended or adjusted under 35 U.S.C. 154(b) by 38 days.

(21) Appl. No.: 09/653,605

(22) Filed: Aug. 31, 2000

(51) Int. Cl.[7] ..... A01H 5/00
(52) U.S. Cl. ..... Plt./364

(58) Field of Search ..... Plt./364

*Primary Examiner*—Bruce R. Campell
*Assistant Examiner*—A Para
(74) *Attorney, Agent, or Firm*—C. A. Whealy

(57) ABSTRACT

A distinct cultivar of Spathiphyllum plant named Jumbo, characterized by its tall, upright plants; large leaves that are held upright to horizontal to the petiole; moderate vigor and growth rate; numerous large white spathes that are positioned above the foliage on strong and erect peduncles; and long-lasting inflorescences.

4 Drawing Sheets

BACKGROUND OF THE INVENTION

The present Invention relates to a new and distinct cultivar of Spathiphyllum plant, botanically known as Spathiphyllum hybrid, and hereinafter referred to by the cultivar name Jumbo.

The new cultivar is a product of a planned and controlled breeding program conducted by the Inventor in de Kwakel, The Netherlands. The objective of the breeding program is to create new Spathiphyllum cultivars with dense growth habit and attractive leaf and spathe coloration and form.

The new cultivar originated from a cross by the Inventor between the Spathiphyllum hybrid cultivar Ceres, disclosed in U.S. Plant Pat. No. 8,844, and an unnamed selection of *Spathiphyllum cochlerispathum* as the male or pollen parent. The cultivar Jumbo was discovered and selected by the Inventor in April, 1995 as a plant within the progeny of the stated cross in a controlled environment in de Kwakel, The Netherlands.

In side-by-side comparisons conducted by the Inventor in de Kwakel, The Netherlands, the following differences between the new Spathiphyllum and the female parent, the cultivar Ceres, have been observed:

1. Plants of the new Spathiphyllum are larger than plants of the cultivar Ceres.
2. Plants of the new Spathiphyllum are not as freely branching as plants of the cultivar Ceres.
3. Leaves of plants of the new Spathiphyllum are lighter green and more oval-shaped than leaves of plants of the cultivar Ceres.
4. Plants of the new Spathiphyllum have larger but fewer inflorescences than plants of the cultivar Ceres.

In side-by-side comparisons conducted by the Inventor in de Kwakel, The Netherlands, the following differences between the new Spathiphyllum and the male parent, an unnamed selection of *Spathiphyllum cochlerispathum*, have been observed:

1. Plants of the new Spathiphyllum are smaller than plants of the unnamed selection of *Spathiphyllum cochlerispathum.*
2. Plants of the new Spathiphyllum are more freely branching and are denser than plants of the unnamed selection of *Spathiphyllum cochlerispathum.*

3. Leaves of plants of the new Spathiphyllum are lighter green and more oval-shaped than leaves of plants of the unnamed selection of *Spathiphyllum cochlerispathum.*
4 Spathes of plants of the new Spathiphyllum are white whereas spathes of plants of the unnamed selection of *Spathiphyllum cochlerispathum* are dark green in color.

Asexual propagation by divisions and tissue-culture of the new cultivar at de Kwakel, The Netherlands, has shown that the unique features of this new Spathiphyllum plant are stable and reproduced true to type in successive generations of asexual propagation.

BRIEF SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of Jumbo. These characteristics in combination distinguish Jumbo as a new and distinct cultivar:

1. Tall, upright plants.
2. Large leaves that are held upright to horizontal to the petiole.
3. Moderate vigor and growth rate.
4. Numerous large white spathes that are positioned above the foliage on strong and erect peduncles.
5. Long-lasting inflorescences.

Plants of the new Spathiphyllum can be compared to plants of the commercial Spathiphyllum cultivar Sensation (not patented). In side-by-side comparisons conducted by the Inventor in de Kwakel, The Netherlands, the following differences between the new Spathiphyllum and the cultivar Sensation have been observed:

1. Plants of the new Spathiphyllum are more freely branching and denser than plants of the cultivar Sensation.
2. Leaves of plants of the new Spathiphyllum are lighter green than leaves of plants of the cultivar Sensation.

3. Spathes of plants of the new Spathiphyllum are brighter white and more oval in shape than spathes of plants of the cultivar Sensation.
4. Plants of the new Spathiphyllum flower earlier than plants of the cultivar Sensation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Spathiphyllum.

The photograph on the first sheet comprises a side perspective view of a typical potted plant of 'Jumbo'.

The photograph at the top of the second sheet comprises a close-up view of the front surface of a typical inflorescence of 'Jumbo'.

The photograph at the bottom of the second sheet comprises a close-up view of the rear surface of a typical inflorescence of 'Jumbo'.

The photograph on the left of the third sheet comprises a close-up view of the upper surface of a typical young leaf of 'Jumbo'.

The photograph on the right of the third sheet comprises a close-up view of the lower surface of a typical young leaf of 'Jumbo'.

The photograph on the left of the fourth sheet comprises a close-up view of the upper surface of a typical mature leaf of 'Jumbo'.

The photograph on the right of the fourth sheet comprises a close-up view of the lower surface of a typical mature leaf of 'Jumbo'.

DETAILED BOTANICAL DESCRIPTION

In the following description, color references are made to The Royal Horticultural Society Colour Chart except where general terms of ordinary dictionary significance are used. The following observations and measurements describe 14-month old plants grown in de Kwakel, The Netherlands, in a glass greenhouse under typical commercial conditions with day and night temperatures averaging 22 to 19° C., respectively, and light levels of about 22,000 to 28,000 lux.

Botanical classification: Spathiphyllum hybrid cultivar Jumbo.

Parentage:

*Female parent.*—Spathiphyllum hybrid cultivar Ceres, disclosed in U.S. Plant Pat. No. 8,844.

*Male parent.*—Unnamed selection of *Spathiphyllum cochlerispathum.*

Propagation:

*Type.*—By tissue culture.

*Time to initiate roots, tissue-cultured microcutting.*—About 15 days at 23° C.

*Root description.*—Freely branching, numerous fleshly lateral roots.

Plant description:

*Plant shape.*—Upright, inverted triangle, symmetrical.

*Growth habit.*—Erect when young, becoming more outwardly arching as leaves develop. Appropriate for 21 to 35-cm containers.

*Plant height.*—About 90 cm.

*Plant vigor.*—Moderately vigorous.

*Growth rate.*—Moderate.

*Time to finishing.*—About 14 months are required to produce a finished 21-cm plant from a rooted tissue-cultured plantlet.

*Foliage description.*—Quantity of leaves: About 43. Shape: Lanceolate. Aspect: Mature leaves held upright to perpendicular to petiole. Length: About 43.5 cm. Width: About 26 cm. Apex: Apiculate, apex is curved. Base: Attenuate. Margin: Entire. Texture: Glabrous and slightly glossy, veins slightly sunken; rugose. Petiole: Length: About 37.5 cm. Diameter: About 2 cm. Geniculum: Length: About 3.75 cm. Diameter: About 5 mm. Angle: Straight. Color: Young, upper surface: Close to 144A. Young, lower surface: Close to 138B to 138C. Mature, upper surface: Close to 137B to 137C. Mature, lower surface: Close to 138A to 138B. Venation, upper surface: Midvein same as leaf surface; lateral veins, close to 144A. Venation, lower surface: Midvein same as leaf surface; lateral veins, close to 144B. Petiole: Close to 138A. Geniculum: 144B.

Inflorescence description:

*Inflorescence arrangement.*—Large concave spathes with spadices held above the foliage. Numerous flowers arise from leaf axils. Flowering continuous. Flowers persistent.

*Longevity.*—Spathes are long-lasting, generally maintaining white color for about six weeks on the plant depending on light and temperature levels.

*Spathe.*—Appearance: Leathery. Angle: Erect, upright. Shape: Lanceolate. Apex: Apiculate; elongated apex cirrhous. Base: Cuneate. Margin: Entire. Length: About 30 cm. Width: About 16.5 cm. Aspect: Concave, curving towards the spadix. Color: Immature spathes, both surfaces: 144A. Mature spathes, front surface: 155A; apex and distal midvein, green, 144A. Mature spathes, rear surface: 155A; midvein, 137D to 144A; lateral veins, 145A.

*Spadix.*—Axis: Longitudinal. Cross section: Rounded. Length: About 14.5 cm. Diameter: About 2.5 cm. Color: 158D.

*Flowers.*—Quantity per spadix: About 600. Shape: Conical. Size: About 2 mm. Stigma shape: Rounded. Pollen color: Mature, 158D; after senescence, 159A.

*Peduncle.*—Aspect: Strong and erect. Length: About 59 cm. Diameter: About 6 mm. Color: 138A.

*Seed.*—Seed development has not been observed.

Disease resistance: Resistance to known Spathiphyllum diseases has not been observed on plants of the new Spathiphyllum.

It is claimed:

1. A new and distinct cultivar of Spathiphyllum plant named Jumbo, as illustrated and described.

* * * * *

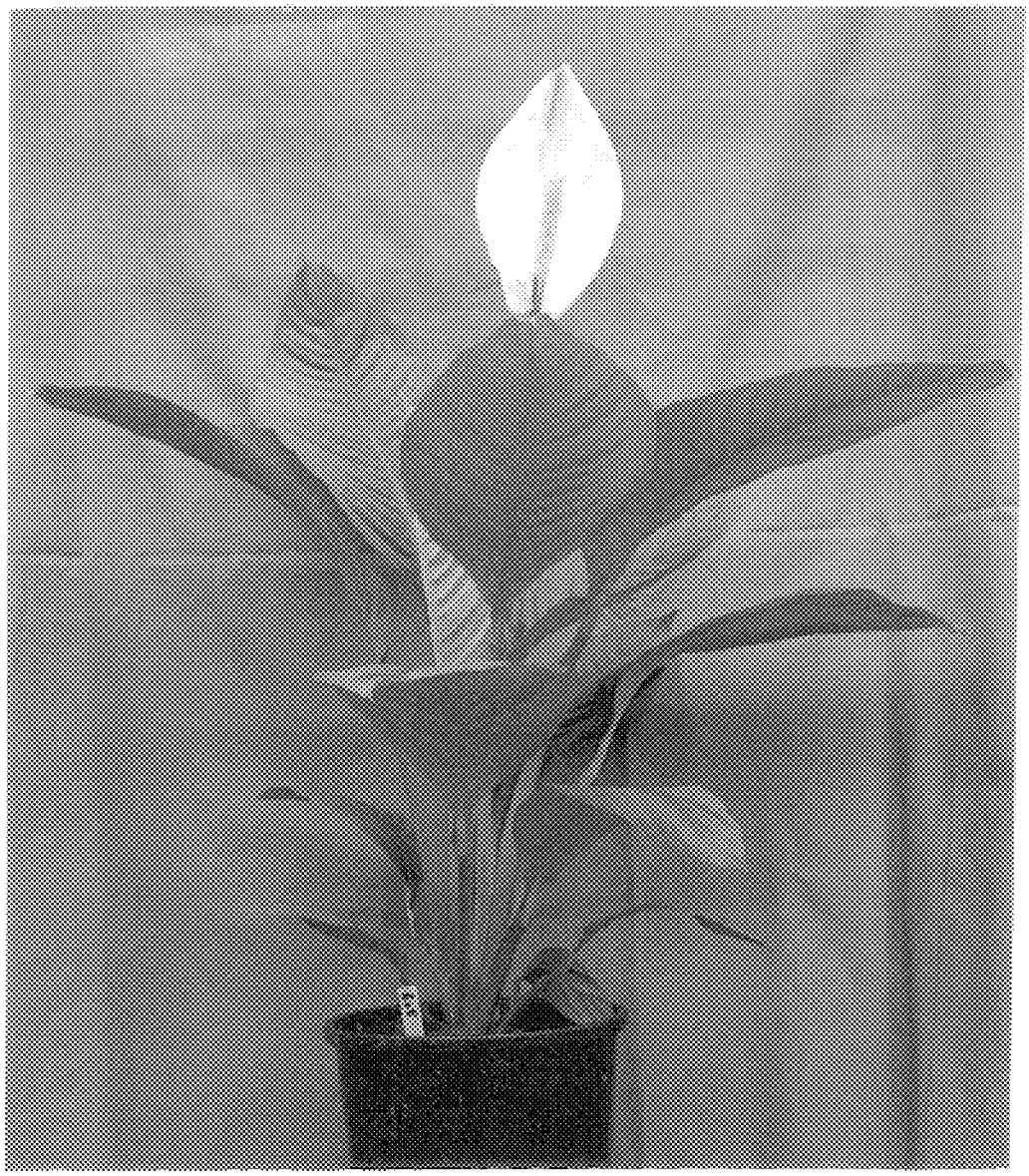

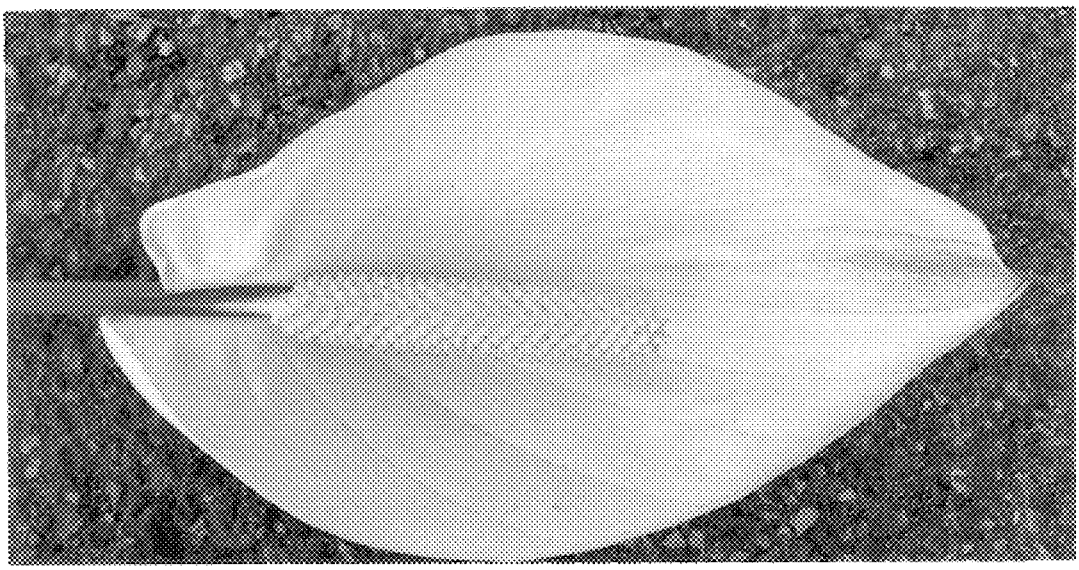
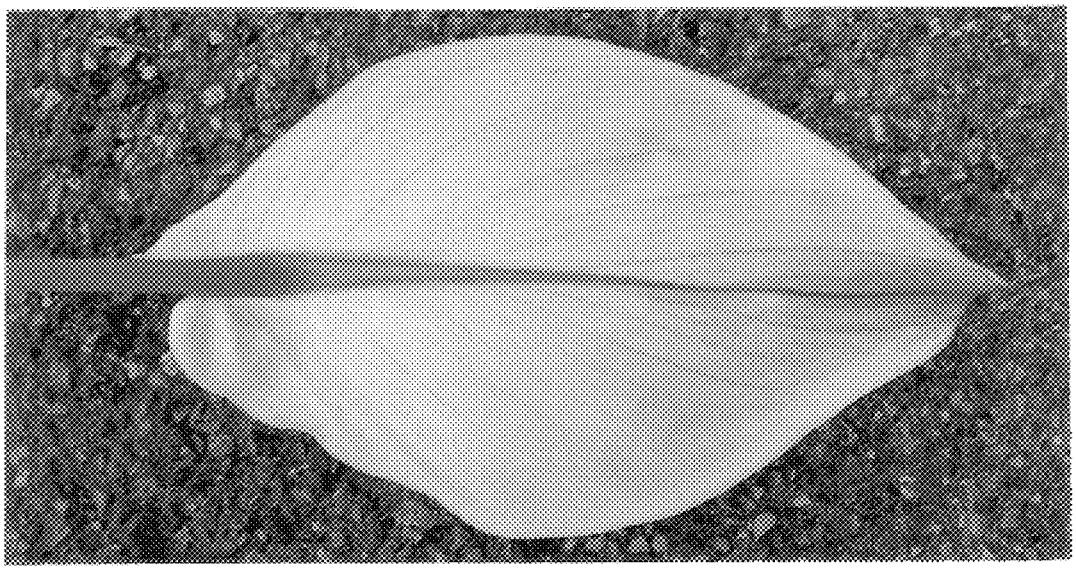

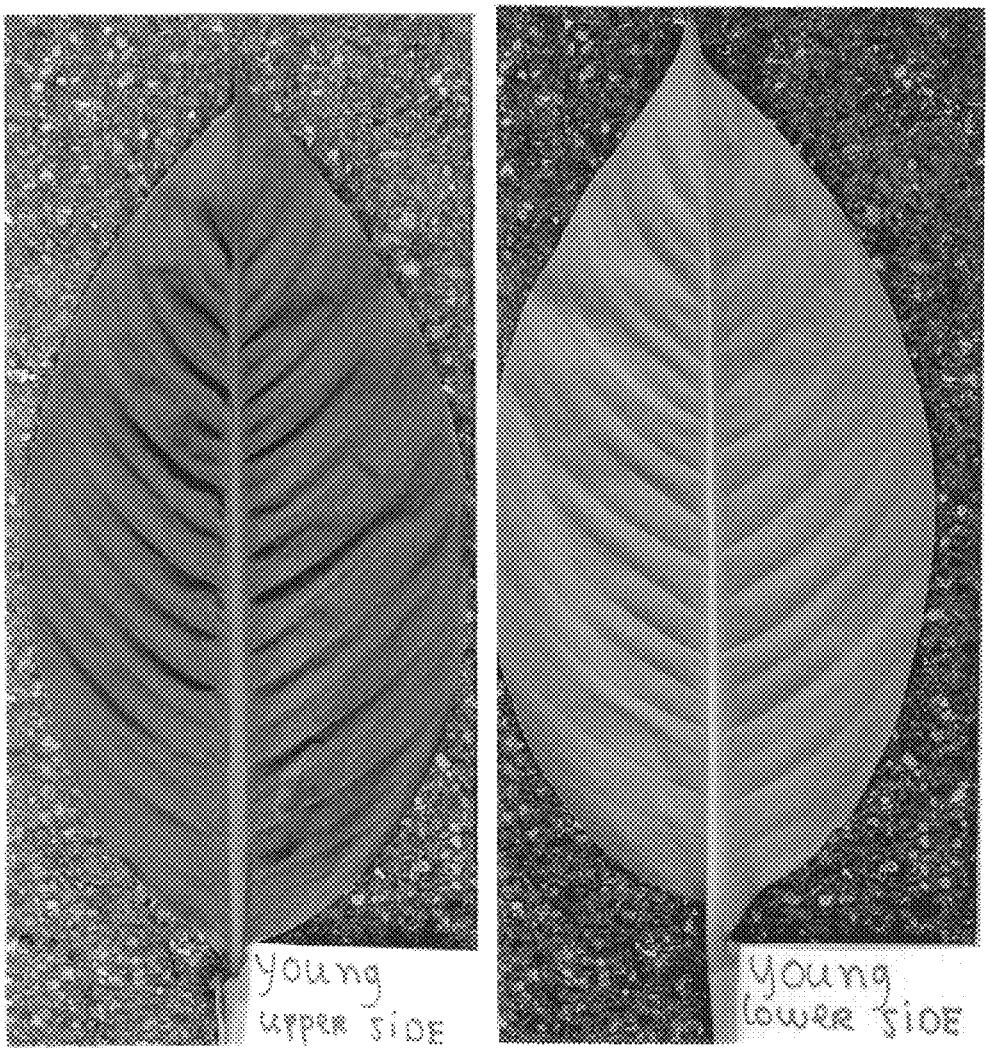
young
upper side
young
lower side

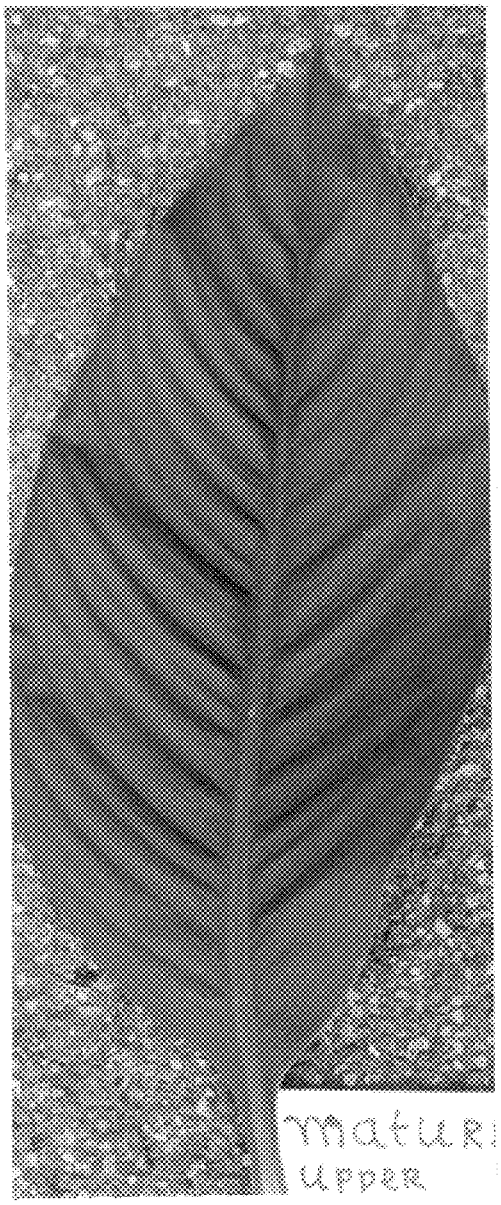
mature
upper
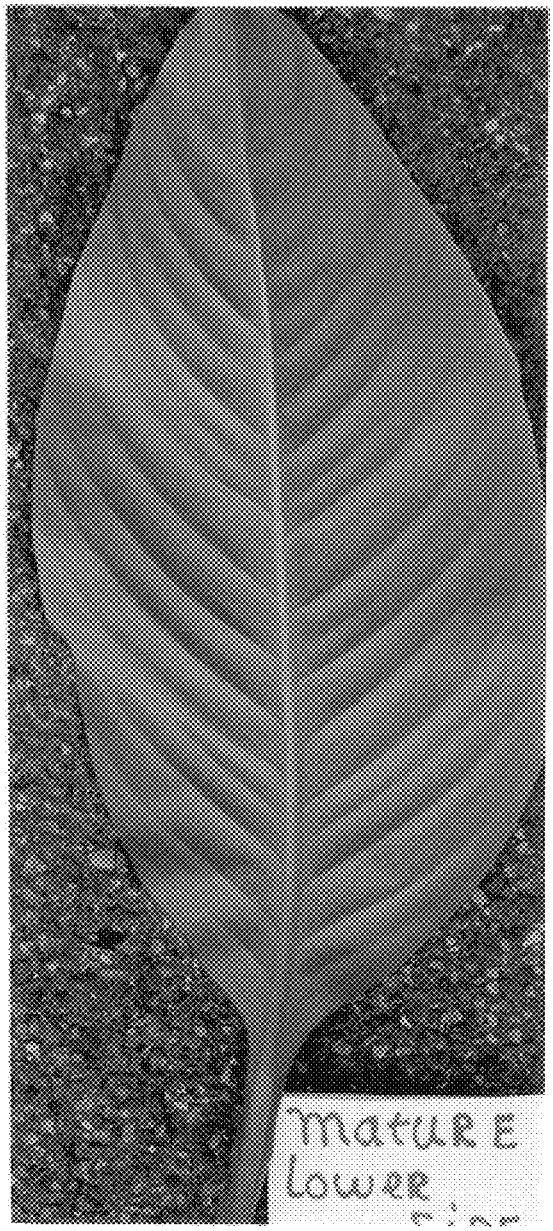
mature
lower